(12) United States Patent
Bivens et al.

(10) Patent No.: US 6,783,691 B1
(45) Date of Patent: Aug. 31, 2004

(54) COMPOSITIONS OF DIFLUOROMETHANE, PENTAFLUOROETHANE, 1,1,1,2-TETRAFLUOROETHANE AND HYDROCARBONS

(75) Inventors: Donald Bernard Bivens, Kennett Square, PA (US); Barbara Haviland Minor, Elkton, MD (US); Akimichi Yokozeki, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/528,964

(22) Filed: Mar. 20, 2000

Related U.S. Application Data

(60) Provisional application No. 60/125,510, filed on Mar. 22, 1999.

(51) Int. Cl.$^7$ .................................................. C09K 5/04
(52) U.S. Cl. ........................................................ 252/67
(58) Field of Search ...................................... 252/67, 68

(56) References Cited

U.S. PATENT DOCUMENTS

| | | | |
|---|---|---|---|
| 5,185,094 A | 2/1993 | Shiflett | 252/67 |
| 5,616,276 A | 4/1997 | Bivens et al. | 252/67 |
| 5,688,432 A | 11/1997 | Pearson | 252/67 |

FOREIGN PATENT DOCUMENTS

| | | | | |
|---|---|---|---|---|
| DE | 42 26 431 A1 | 2/1994 | | C09K/5/04 |
| EP | 0 659 862 A | 6/1995 | | C09K/5/04 |
| JP | 94220430 | 8/1994 | | C09K/5/00 |
| JP | 97025480 | 1/1997 | | C09K/5/04 |
| JP | 9-208940 | * 8/1997 | | |
| WO | WO 96/03473 | 2/1996 | | C09K/5/04 |
| WO | WO 97/15637 | 5/1997 | | C09K/5/04 |

* cited by examiner

*Primary Examiner*—John R. Hardee
(74) *Attorney, Agent, or Firm*—Mark A. Edwards; Chyrrea J. Sebree

(57) ABSTRACT

The present invention relates to azeotrope-like compression refrigerant compositions consisting essentially of difluoromethane (HFC-32), pentafluoroethane (HFC-125), 1,1,1,2-tetrafluoroethane (HFC-134a) and 0.5–5 weight percent of a hydrocarbon selected from the group consisting of: n-butane; isobutane; n-butane and 2-methylbutane; n-butane and n-pentane; isobutane and 2-methylbutane; and isobutane and n-pentane.

6 Claims, No Drawings

COMPOSITIONS OF DIFLUOROMETHANE, PENTAFLUOROETHANE, 1,1,1,2-TETRAFLUOROETHANE AND HYDROCARBONS

CROSS REFERENCE TO RELATED APPLICATIONS

This application claims the priority benefit of U.S. provisional application No. 60/125,510, filed Mar. 22, 1999.

FIELD OF THE INVENTION

The present invention relates to azeotrope-like compositions consisting essentially of difluoromethane, pentafluoroethane, 1,1,1,2-tetrafluoroethane and a hydrocarbon selected from the group consisting of: n-butane; isobutane; n-butane and 2-methylbutane; n-butane and n-pentane; isobutane and 2-methylbutane; and isobutane and n-pentane.

BACKGROUND

In recent years it has been pointed out that certain kinds of fluorinated hydrocarbon refrigerants released into the atmosphere may adversely affect the stratospheric ozone layer. Although this proposition has not yet been completely established, there is a movement toward control of the use and the production of certain chlorofluorocarbons (CFCs) and hydrochlorofluorocarbons (HCFCs) under an international agreement. Accordingly, there is a demand for the development of refrigerants that have a lower ozone depletion potential than conventional CFC and HCFC-based refrigerants while still achieving acceptable performance in refrigeration applications. Hydrofluorocarbons (HFCs) are gaining acceptance as replacements for CFCs and HCFCs as HFCs contain no chlorine and, therefore, have zero ozone depletion potential.

Mineral oils and alkylbenzenes have been conventionally used as lubricants in CFC-based refrigeration systems. However, the lack of solubility of these lubricants in HFC-based refrigerants has precluded their use and necessitated development and use of alternative lubricants for HFC-based refrigeration systems, which utilize polyalkylene glycols (PAGs) and polyol esters (POEs). A lubricant change from mineral oil or alkyl benzene to POE or PAG lubricants (which increases expenses in the refrigeration indusrty) is required when the HFC mixtures are used to replace CFC-based refrigerants. While the PAGs and POEs are suitable lubricants for HFC-based refrigeration systems, they are extremely hygroscopic and can absorb several thousand ppm (parts per million) of water upon exposure to moist air. This absorbed moisture leads to problems in the refrigeration system, such as formation of acids which causes corrosion of the refrigeration system, and the formation of intractable sludges. Conversely, mineral oils and alkylbenzenes are much less hygroscopic and have low solubility, less than 100 ppm, for water. Additionally, PAG and POE lubricants are considerably more expensive than the hydrocarbon lubricants, typically on the order of three to six times more expensive. Consequently, there is a need and an opportunity to resolve this solubility problem so that the refrigeration industry may utilize mineral oil and alkylbenzene lubricants with HFC-based refrigerants.

In refrigeration apparatus, refrigerant may be lost during operation through leaks in shaft seals, hose connections, soldered joints and broken lines. In addition, the refrigerant may be released to the atmosphere during maintenance procedures on refrigeration equipment. If the refrigerant is not a pure component or an azeotropic or azeotrope-like composition, the refrigerant composition may change when leaked or discharged to the atmosphere from the refrigeration apparatus, which may cause the refrigerant remaining in the equipment to become flammable or to exhibit unacceptable refrigeration performance. Accordingly, it is desirable to use as a refrigerant a single fluorinated hydrocarbon or an azeotropic or azeotrope-like composition which fractionates to a negilgible degree upon leak from a refrigeration apparatus.

In refrigeration applications where the potential of fire or fire's toxic byproducts are a concern, it is desirable for refrigerant compositions to be nonflammable in both liquid and vapor phases, when charging fresh refrigerant to a system or after refrigerant has leaked from a system.

Accordingly, there is a need in the refrigeration industry for compositions that are non-ozone depleting, nonflammable, and essentially non-fractionating azeotrope-like compositions. Additionally, there is a need in the refrigeration industry for compositions that offer improved return of conventional-refrigeration lubricating oils from non-compressor to compressor zones in compression-refrigeration apparatus, as well as superior refrigeration performance.

SUMMARY

The compositions of the present invention satsify the aforementioned needs confronting the refrigeration industry. The present compositions are useful as refrigerants, and in particular as HCFC-22 alternatives. Unlike compositions containing propane and pentane, compositions of the present invention are non-flammable in both liquid and vapor phases—as intially formulated and during leakage. The present invention is directed to azeotrope-like compositions consisting essentially of from about 1 to about 19 weight percent difluoromethane (HFC-32), from about 25 to about 60 weight percent pentafluoroethane (HFC-125), from about 24 to about 60 weight percent 1,1,1,2-tetrafluoroethane (HFC-134a) and from about 0.5 to about 5 weight percent of a hydrocarbon, wherein said hydrocarbon is selected from the group consisting of: n-butane; isobutane; n-butane and 2-methylbutane; n-butane and n-pentane; isobutane and 2-methylbutane; and isobutane and n-pentane.

DETAILED DESCRIPTION

The azeotrope-like compositions of the present invention consist essentially of difluoromethane (HFC-32, $CH_2F_2$, normal boiling point of −51.7° C.), pentafluoroethane (HFC-125, $CF_3CHF_2$, normal boiling point of −48.5° C.), 1,1,1,2-tetrafluoroethane (HFC-134a, $CF_3CHF_2$, normal boiling point of −26.1° C.) and a hydrocarbon selected from the group consisting of: n-butane ($CH_3CH_2CH_2CH_3$, normal boiling point of −0.5° C.); isobutane ($CH(CH_3)_3$, normal boiling point of −11.8° C.); n-butane and 2-methylbutane ($CH_3CH_2CH(CH_3)_2$, normal boiling point of 27.9° C.); n-butane and n-pentane ($CH_3CH_2CH_2CH_2CH_3$, normal boiling point of 35.9° C.); isobutane and 2-methylbutane; and isobutane and n-pentane.

The azeotrope-like compositions of the present invention consist essentially of from about 1 to about 19 weight percent difluoromethane, from about 25 to about 60 weight percent pentafluoroethane, from about 24 to about 60 weight percent 1,1,1,2-tetrafluoroethane and from about 0.5 to about 5 weight percent of a hydrocarbon, said hydrocarbon selected from the group consisting of: n-butane; isobutane; n-butane and 2-methylbutane; n-butane and n-pentane;

isobutane and 2-methylbutane; and isobutane and n-pentane. The preferred azeotrope-like compositions of the present invention consist essentially of from about 1 to about 15 weight percent difluoromethane, from about 30 to about 50 weight percent pentafluoroethane, from about 30 to about 50 weight percent 1,1,1,2-tetrafluoroethane and from about 1 to about 4 weight percent of the aforementioned hydrocarbons. The most preferred azeotrope-like compositions of the present invention consist essentially of 1–9 weight percent difluoromethane (HFC-32), 30–50 weight percent pentafluoroethane (HFC-125), 30–50 weight percent 1,1,1,2-tetrafluoroethane (HFC-134a) and 1–4 weight percent of the aforementioned hydrocarbons.

As previously stated, in refrigeration apparatus, refrigerant may be lost during operation through leaks in shaft seals, hose connections, soldered joints and broken lines. Additionally, the refrigerant may be released to the atmosphere during maintenance procedures on refrigeration equipment. If the refrigerant is not a pure component or an azeotropic or azeotrope-like composition, the refrigerant composition may change when leaked or discharged to the atmosphere from the refrigeration apparatus, which may cause the refrigerant remaining in the equipment to become flammable or to exhibit unacceptable refrigeration performance. Accordingly, it is desirable to use as a refrigerant a single fluorinated hydrocarbon or an azeotropic or azeotrope-like composition, such as the present invention, which fractionates to a negilgible degree upon leak from a refrigeration apparatus.

By azeotrope-like composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same composition as the liquid from which it was evaporated or distilled, that is, the admixture distills/refluxes without substantial composition change. Another way to characterize an azeotrope-like composition is that the bubble point vapor pressure and the dew point vapor pressure of the composition at a particular temperature are substantially the same. Herein, a composition is azeotrope-like if, after 50 weight percent of the composition is removed, such as by evaporation or boiling off, the difference in vapor pressure between the original composition and the composition remaining after 50 weight percent of the original composition has been removed is less than about 10 percent.

By effective amount is meant the amount of each component of the inventive compositions which, when combined, results in the formation of an azeotrope-like composition. This definition includes the amounts of each component, which amounts may vary depending on the pressure applied to the composition so long as the azeotrope-like compositions continue to exist at the different pressures, but with possible different boiling points. Therefore, effective amount includes the amounts, such as may be expressed in weight percentages, of each component of the compositions of the instant invention, which form an azeotrope-like composition at temperatures or pressures other than as described herein.

The azeotrope-like compositions of the present invention can be prepared by any convenient method including mixing or combining effective amounts of components. A preferred method is to weigh the desired component amounts, and thereafter, combine them in an appropriate container.

A surprising result, and an important feature of the present compositions, is that they remain nonflammable in both the vapor and liquid phases before and after the compositions leak from a container. Based on standard flammability test method ASTM 681 at 100° C., the following flammability limits have been determined:

| Composition | Flammability Limit (Wt %) |
| --- | --- |
| HFC-125/HFC-32 | 57% HFC-32 |
| HFC-134a/HFC-32 | 33% HFC-32 |
| HFC-125/n-butane | 6% n-butane |
| HFC-134a/n-butane | 3% n-butane |

The data show compositions with a higher amount of HFC-125 can tolerate more hydrocarbon and still be nonflammable. Also, HFC-32 is about 10 times less flammable than hydrocarbons. To give an indication of mixture flammability, the following formula gives an approximation of the "total equivalent hydrocarbon" (THE) present in mixtures that contain both HFC-32 and hydrocarbons: TEH=HC+R32/10, where TEH=Total Equivalent Hydrocarbon in weight percent, HC=weight percent hydrocarbon in a mixture, and R32=weight percent HFC-32 in a mixture. For the compositions of the present invention, it is useful to relate the amount of HFC-125 in the mixture to flammability because HFC-125 has some degree of flame suppression. Table 1 indicates the flammability limit of a mixture containing both HFC-32 and hydrocarbons based on HFC-125 composition and TEH.

TABLE 1

| Weight Percent HFC-125 in HFC-32/HFC-125/HFC-134a/HC Mixture | Maximum Weight Percent TEH To Be Nonflammable |
| --- | --- |
| 10 | 3.0 |
| 20 | 3.3 |
| 30 | 3.7 |
| 40 | 4.0 |
| 50 | 4.3 |
| 60 | 4.7 |
| 70 | 5.0 |
| 80 | 5.5 |
| 90 | 6.0 |

Additives known in the refrigerants field such as lubricants, corrosion inhibitors, surfactants, stabilizers, antifoam agents, dyes and other appropriate materials may be added to, and used in the presence of, the present compositions of the invention for a variety of purposes, provide that such additives do not have an adverse influence on the present compositions for their intended application or change the basic and novel characteristics of the present invention as claimed.

Although the present specification is directed to use of the present azeotrope-like compositions as compression refrigerants, the present compositions may also find utility as cleaning agents, expansion agents for polyolefins and polyurethanes (polymer foam blowing agents), aerosol propellants, heat transfer media, gaseous dielectrics, power cycle working fluids, polymerization media, particulate removal fluids, carrier fluids, buffing abrasive agents and displacement drying agents.

EXAMPLES

Specific examples illustrating the present invention are given below. Unless otherwise stated therein, all percentages are by weight.

Example 1

Impact of Vapor Leakage on Compositional Change at 25° C. of a HFC-32, HFC-125, HFC-134a, n-butane and Optionally 2-methylbutane or n-pentane Composition A vessel is charged to 90 volume % full with an initial composition of HFC-32, HFC-125, HFC-134a, n-butane and optionally 2-methylbutane or n-pentane at 25° C. The initial liquid and vapor compositions are measured by gas chromatography. The composition is allowed to leak from the vessel, while the temperature is held constant at 25° C., until 50 weight percent of the initial composition is removed, at which time the liquid and vapor compositions remaining in the vessel are again measured. The vessel is than allowed to continue to leak until all the liquid is gone. In all cases, liquid was gone after about 97 wt % was removed. The results are summarized in Table 2 below. All compositions are given in weight %.

TABLE 2

|  | Initial Liquid | Initial Vapor | 50% Leak-Liquid | 50% Leak-Vapor | 97% Leak-Liquid | 97% Leak-Vapor |
|---|---|---|---|---|---|---|
| HFC-32 | 9.0 | 12.8 | 6.5 | 9.9 | 1.0 | 1.9 |
| HFC-125 | 46.0 | 55.6 | 38.8 | 49.9 | 10.7 | 18.1 |
| HFC-134a | 42.5 | 29.1 | 52.3 | 37.6 | 87.3 | 78.4 |
| n-butane | 2.5 | 2.5 | 2.4 | 2.6 | 1.0 | 1.6 |
| The | 3.4 | 3.8 | 3.0 | 3.6 | 1.1 | 1.8 |
| HFC-32 | 10.0 | 14.2 | 7.3 | 10.9 | 1.1 | 2.1 |
| HFC-125 | 45.0 | 54.3 | 37.9 | 48.8 | 10.4 | 17.6 |
| HFC-134a | 42.5 | 29.0 | 52.4 | 37.6 | 87.5 | 78.7 |
| n-butane | 2.5 | 2.5 | 2.4 | 2.7 | 1.0 | 1.6 |
| The | 3.5 | 3.9 | 3.1 | 3.8 | 1.1 | 1.8 |
| HFC-32 | 10.0 | 13.9 | 7.3 | 11.0 | 1.0 | 1.9 |
| HFC-125 | 45.0 | 52.3 | 38.8 | 49.2 | 10.3 | 17.7 |
| HFC-134a | 42.5 | 28.3 | 52.9 | 37.3 | 88.7 | 80.3 |
| Propane | 2.5 | 5.5 | 1.0 | 2.5 | 0.0 | 0.1 |
| The | 3.5 | 6.9* | 1.7 | 3.6 | 0.1 | 0.3 |
| HFC-32 | 10.0 | 14.4 | 7.1 | 11.0 | 0.7 | 1.4 |
| HFC-125 | 45.0 | 55.1 | 37.3 | 49.1 | 7.6 | 14.1 |
| HFC-134a | 42.5 | 29.3 | 51.9 | 38.2 | 72.7 | 78.5 |
| n-pentane | 2.5 | 1.2 | 3.6 | 1.7 | 19.0 | 6.0 |
| The | 3.5 | 2.6 | 4.3* | 2.8 | 19.1* | 6.1* |
| HFC-32 | 10 | 14.2 | 7.3 | 10.9 | 1.0 | 2.0 |
| HFC-125 | 45 | 54.5 | 37.8 | 48.9 | 10.1 | 17.1 |
| HFC-134a | 42.5 | 29.0 | 52.3 | 37.7 | 86.1 | 78.2 |
| n-butane | 2.0 | 2.0 | 1.9 | 2.1 | 0.9 | 1.4 |
| 2-mbutane | 0.5 | 0.3 | 0.7 | 0.4 | 1.9 | 1.3 |
| The | 3.5 | 3.7 | 3.3 | 3.6 | 2.9 | 2.9 |
| HFC-32 | 5.0 | 8.0 | 3.2 | 5.4 | 0.2 | 0.5 |
| HFC-125 | 32.2 | 43.9 | 24.1 | 35.5 | 3.7 | 6.8 |
| HFC-134a | 60.0 | 45.4 | 69.9 | 56.3 | 93.1 | 90.0 |
| n-butane | 2.0 | 2.3 | 1.7 | 2.2 | 0.5 | 0.8 |
| 2-mbutane | 0.8 | 0.4 | 1.1 | 0.6 | 2.5 | 1.9 |
| The | 2.9 | 3.5 | 3.1 | 3.3 | 3.0 | 2.8 |
| HFC-32 | 5 | 7.2 | 3.6 | 5.5 | 0.5 | 1.0 |
| HFC-125 | 50 | 61.0 | 41.8 | 54.3 | 11.2 | 18.8 |
| HFC-134a | 42.7 | 29.7 | 52.2 | 38.0 | 85.1 | 77.5 |
| n-butane | 1.8 | 1.9 | 1.7 | 1.9 | 0.9 | 1.2 |
| n-pentane | 0.5 | 0.2 | 0.7 | 0.3 | 2.3 | 1.5 |
| THE | 2.8 | 2.9 | 2.8 | 2.9 | 3.2 | 2.8 |

*Compositions are flammable based on TEH analysis

When TEH values of this Example are compared to Table 1, results show compositions of the precent invention are essentially nonflammable, initially and as contents are completely leaked out of the container. Data also show addition of a higher boiling hydrocarbon such as 2-methylbutane reduces initial vapor phase flammability when compared to using only n-butane. Compositions containing propane are flammable initially in the vapor phase and compositions containing n-pentane become flammable in the liquid and/or vapor phases as liquid is removed.

Example 2

Impact of Vapor Leakage on Compositional Change at 25° C. of a HFC-32, HFC-125, HFC-134a, Isobutane and Optionally 2-methylbutane or n-pentane Composition A vessel is charged to 90 volume % full with an initial composition of HFC-32, HFC-125, HFC-134a, isobutane and optionally 2-methylbutane or n-pentane at 25° C. The initial liquid and vapor compositions are measured by gas chromatography. The composition is allowed to leak from the vessel, while the temperature is held constant at 25° C., until 50 weight percent of the initial composition is removed, at which time the liquid and vapor compositions remaining in the vessel are again measured. The vessel is than allowed to continue to leak until all the liquid is gone. In all cases, liquid was gone after about 97 wt % was removed. The results are summarized in Table 3 below. All compositions are given in weight %.

TABLE 3

|  | Initial Liquid | Initial Vapor | 50% Leak-Liquid | 50% Leak-Vapor | 97% Leak-Liquid | 97% Leak-Vapor |
|---|---|---|---|---|---|---|
| HFC-32 | 10.0 | 12.7 | 6.5 | 9.8 | 1.0 | 1.9 |
| HFC-125 | 45.0 | 55.3 | 39.0 | 49.9 | 10.7 | 18.1 |
| HFC-134a | 42.5 | 29.0 | 52.4 | 37.5 | 88.0 | 79.3 |
| Isobutane | 2.5 | 3.0 | 2.1 | 2.8 | 0.3 | 0.7 |
| The | 3.5 | 4.3 | 2.7 | 3.8 | 0.4 | 0.9 |
| HFC-32 | 10.0 | 14.0 | 7.4 | 10.9 | 1.1 | 2.2 |
| HFC-125 | 47.0 | 55.7 | 40.2 | 50.8 | 11.8 | 19.8 |
| HFC-134a | 40.5 | 27.3 | 50.3 | 35.5 | 86.7 | 77.2 |
| Isobutane | 2.5 | 3.0 | 2.1 | 2.8 | 0.4 | 0.8 |
| The | 3.5 | 4.4 | 2.8 | 3.9 | 0.5 | 1.0 |
| HFC-32 | 10.0 | 14.2 | 7.2 | 10.9 | 1.0 | 2.0 |
| HFC-125 | 45.5 | 54.2 | 38.0 | 48.9 | 10.0 | 17.0 |
| HFC-134a | 42.5 | 29.0 | 52.4 | 37.6 | 86.4 | 78.9 |
| Isobutane | 2.0 | 2.4 | 1.7 | 2.2 | 0.4 | 0.6 |
| n-pentane | 0.5 | 0.2 | 0.7 | 0.4 | 2.2 | 1.5 |
| The | 3.5 | 4.0 | 3.1 | 3.7 | 2.7 | 2.3 |
| HFC-32 | 15.0 | 23.0 | 9.9 | 16.5 | 0.8 | 1.6 |
| HFC-125 | 24.0 | 32.3 | 18.1 | 26.6 | 2.7 | 5.0 |
| HFC-134a | 60.0 | 43.6 | 71.1 | 55.9 | 95.4 | 92.4 |
| Isobutane | 0.5 | 0.8 | 0.3 | 0.6 | 0.0 | 0.0 |
| 2-mbutane | 0.5 | 0.3 | 0.6 | 0.4 | 1.1 | 1.0 |
| The | 2.5 | 3.4 | 1.9 | 2.6 | 1.2 | 1.2 |
| HFC-32 | 19 | 24.6 | 15.1 | 20.7 | 3.7 | 6.5 |
| HFC-125 | 50 | 55.8 | 45.3 | 53.2 | 19.0 | 29.2 |
| HFC-134a | 30 | 18.8 | 38.5 | 25.3 | 74.9 | 62.7 |
| Isobutane | 0.5 | 0.6 | 0.4 | 0.5 | 0.1 | 0.2 |
| n-pentane | 0.5 | 0.2 | 0.7 | 0.3 | 2.3 | 1.4 |
| THE | 2.9 | 3.3 | 2.6 | 2.9 | 2.8 | 2.2 |

When TEH values of this Example are compared to Table 1, results show compositions are essentially nonflammable, initially and as contents are completely leaked out of the container. Data also show addition of a higher boiling hydrocarbon such as n-pentane reduces initial vapor phase flammability when compared to using only isobutane.

Example 3

Impact of Vapor Leakage on Vapor Pressure at 25° C.

A vessel is charged with an initial composition at 25° C., and the initial vapor pressure of the composition is measured. The composition is allowed to leak from the vessel while the temperature is held constant at 25° C. until 50 weight percent of the initial composition is removed, at which time the vapor pressure of the composition remaining in the vessel is measured. The results are summarized in Table 4 below.

TABLE 4

| Composition (Wt %) | Initial Pressure (kPa) | Pressure After Leak (kPa) | % Change in Pressure |
|---|---|---|---|
| HFC-32/HFC-125/HFC-134/n-butane | | | |
| 1.0/60.0/34.0/5.0 | 1101 | 1042 | 5.4 |
| 19.0/56.5/24.0/0.5 | 1348 | 1272 | 5.6 |
| 9.0/46.0/42.5/2.5 | 1134 | 1044 | 7.9 |
| 5.0/34.0/60.0/1.0 | 979 | 891 | 9.0 |
| 16.0/57.0/24.0/3.0 | 1318 | 1245 | 5.5 |
| 19.0/25.0/51.0/5.0 | 1149 | 1038 | 9.7 |
| 10.0/45.0/42.5/2.5 | 1142 | 1051 | 8.0 |
| HFC-32/HFC-125/HFC-134a/isobutane | | | |
| 1.0/60.0/34.0/5.0 | 1123 | 1065 | 5.2 |
| 19.0/56.5/24.0/0.5 | 1351 | 1275 | 5.6 |
| 9.0/46.0/42.5/2.5 | 1147 | 1055 | 8.0 |
| 5.0/34.0/60.0/1.0 | 985 | 895 | 9.1 |
| 16.0/57.0/24.0/3.0 | 1333 | 1261 | 9.5 |
| 19.0/25.0/51.0/5.0 | 1172 | 1059 | 9.6 |
| 10.0/45.0/42.5/2.5 | 1155 | 1062 | 8.1 |
| 10.0/47.0/40.5/2.5 | 1167 | 1078 | 7.6 |
| HFC-32/HFC-125/HFC-134a/n-butane/2-methylbutane | | | |
| 1.0/60.0/34.0/0.5/4.5 | 1064 | 985 | 7.4 |
| 19.0/56.5/24.0/0.5/0.5 | 1342 | 1264 | 5.8 |
| 9.0/46.0/42.5/1.0/1.5 | 1120 | 1024 | 8.6 |
| 5.0/34.0/60.0/0.5/0.5 | 974 | 885 | 9.1 |
| 16.0/57.0/24.0/2.0/1.0 | 1310 | 1231 | 6.0 |
| 19.0/25.0/51.0/4.5/0.5 | 1145 | 1031 | 10.0 |
| 10.0/45.0/42.5/2.0/0.5 | 1138 | 1044 | 8.3 |
| HFC-32/HFC-125/HFC-134a/n-butane/n-pentane | | | |
| 1.0/60.0/34.0/0.5/4.5 | 1058 | 975 | 7.8 |
| 19.0/56.5/24.0/0.5/0.5 | 1341 | 1262 | 5.9 |
| 9.0/46.0/42.5/1.0/1.5 | 1118 | 1020 | 8.8 |
| 5.0/34.0/60.0/0.5/0.5 | 973 | 885 | 9.0 |
| 16.0/57.0/24.0/2.0/1.0 | 1309 | 1229 | 6.1 |
| 19.0/25.0/51.0/4.5/0.5 | 1145 | 1030 | 10.0 |
| 10.0/45.0/42.5/2.0/0.5 | 1137 | 1043 | 8.3 |
| HFC-32/HFC-125/HFC-134a/isobutane/2-methylbutane | | | |
| 1.0/60.0/34.0/0.5/4.5 | 1066 | 987 | 7.4 |
| 19.0/56.5/24.0/0.5/0.5 | 1345 | 1267 | 5.8 |
| 9.0/46.0/42.5/1.0/1.5 | 1125 | 1028 | 8.6 |
| 5.0/34.0/60.0/0.5/0.5 | 976 | 887 | 9.1 |
| 16.0/57.0/24.0/2.0/1.0 | 1320 | 1242 | 5.9 |
| 19.0/25.0/51.0/4.5/0.5 | 1167 | 1050 | 10.0 |
| 10.0/45.0/42.5/2.0/0.5 | 1147 | 1053 | 8.2 |
| HFC-32/HFC-125/HFC-134a/isobutane/n-pentane | | | |
| 1.0/60.0/34.0/0.5/4.5 | 1060 | 977 | 7.8 |
| 19.0/56.5/24.0/0.5/0.5 | 1344 | 1265 | 5.9 |
| 9.0/46.0/42.5/1.0/1.5 | 1122 | 1024 | 8.7 |
| 5.0/34.0/60.0/0.5/0.5 | 975 | 886 | 9.1 |
| 16.0/57.0/24.0/2.0/1.0 | 1319 | 1238 | 6.1 |
| 19.0/25.0/51.0/4.5/0.5 | 1166 | 1049 | 10.0 |
| 10.0/45.0/42.5/2.0/0.5 | 1147 | 1051 | 8.4 |
| HFC-32/HPC-125/HPC-134a/propane (10.0/45.0/42.5/2.5 | 1247 | 1096 | 12.1 |

The results of this Example show azeotrope-like compositions of the present invention are present as after 50 wt % of an original composition is removed, the vapor pressure of the remaining composition is changed by less than about 10% of the vapor pressure of the original composition, at a temperature of 25° C. Reducing the amount of HFC-32 in the compositions may result in a more azeotrope-like mixture. Compositions containing propane are not azeotrope-like.

Example 4

Effect of Hydrocarbon Addition on Fractionation

A vessel is charged 90% full by volume with an initial composition at 25° C., and the initial vapor pressure of the composition is measured. The composition is allowed to leak from the vessel, while the temperature is held constant at 25° C. until 50 weight percent of the initial composition is removed, at which time the vapor pressure of the composition remaining in the vessel is measured. The results are summarized in Table 5 below.

TABLE 5

| Composition (Wt %) | Initial Pressure (kPa) | Pressure After Leak (kPa) | % Change in Pressure |
|---|---|---|---|
| HFC-32/HFC-125/HFC-134a (refrigerant "R407C") (23/25/52) | 1179 | 1055 | 10.5 |
| HFC-32/HFC-125/HFC-134a (20/40/40) | 1241 | 1135 | 8.5 |
| HFC-32/HFC-125/HFC-134a/n-butane(15/42/41.5/1.5) | 1193 | 1093 | 8.4 |
| HFC-32/HFC-125/HFC-134a/n-butane(10/45/42.5/2.5) | 1142 | 1051 | 8.0 |
| HFC-32/HFC-125/HFC-134a/n-butane(5/48/44/3) | 1083 | 1005 | 7.2 |
| HFC-32/HFC-125/HFC-134a/isobutane(15/42/41.5/1.5) | 1200 | 1099 | 8.4 |
| HFC-32/HFC-125/HFC-134a/isobutane(10/45/42.5/2.5) | 1155 | 1062 | 8.1 |
| HFC-32/HFC-125/HFC-134a/isobutane(5/48/44/3) | 1098 | 1017 | 7.4 |

The results of this Example show that fractionation is reduced; compositions become more azeotrope-like as HFC-32 is replaced with the present hydrocarbons. Compositions of the present invention also have less fractionation than refrigerant composition R407C.

Example 5

Refrigerant Performance

The following table shows the performance of compositions of the present invention. The data are based on the following conditions.

Evaporator temperature 8.9° C.

Condenser temperature 46.1° C.

Subcool temperature 39.4° C.

Return gas temperature 18.3° C.

Compressor clearance volume is 4%

Compressor isentropic efficiency is 75%

Capacity is intended to mean the change in enthalpy of the refrigerant in the evaporator per pound of refrigerant circulated, i.e. the heat removed by the refrigerant in the evaporator per time. Coefficient of Performance (COP) is intended to mean the ratio of the capacity to compressor work, It is a measure of refrigerant energy efficiency. Results are shown in Table 6 below.

TABLE 6

| Composition (wt %) | Evap Press (kPa) | Cond Press (kPa) | Comp Disch. T (° C.) | COP | Capacity (Watts) |
|---|---|---|---|---|---|
| HFC-125/HFC-134a/n-butane (46.5/50.0/3.5) | 572 | 1627 | 65.6 | 5.79 | 5317 |
| HFC-125/HFC-134a/isobutane (32.0/64.0/4.0) | 529 | 1516 | 64.3 | 5.87 | 5014 |
| HFC-32/HFC-125/HFC-134a/n-butane(10.0/45.0/42.5/2.5) | 658 | 1852 | 69.3 | 5.74 | 6058 |
| HFC-32/HFC-125/HFC-134a/n-butane/2-methylbutane (5.0/32.0/60.0/2.0/1.0) | 550 | 1582 | 67.3 | 5.89 | 5287 |
| HFC-32/HFC-125/HFC-134a/n-butane/n-pentane (1.0/60.0/34.0/4.0/1.0) | 634 | 1770 | 65.1 | 5.64 | 5595 |
| HFC-32/HFC-125/HFC134a/isobutane (10.0/47.0/40.5/2.5) | 674 | 1892 | 67.9 | 5.70 | 6111 |
| HFC-32/HFC-125/HFC-134a/isobutane/2-methylbutane (15.0/24.0/60.0/0.5/0.5) | 596 | 1722 | 71.4 | 5.90 | 5829 |
| HFC-32/HFC-125/HFC-134a/isobutane/n-pentane (19.0/50.0/30.0/0.5/0.5) | 754 | 2101 | 71.5 | 5.67 | 6820 |

Results of this Example show that compositions of the present invention exhibit either higher capacity, efficiency or both when compared to compositions which do not contain HFC-32.

Example 6

Oil Return Test with Present Compositions

Oil return was tested in an oil-return apparatus as follows. Liquid refrigerant was fed from a pressurized cylinder through copper tubing to a heater where it was vaporized. The refrigerant vapor then passed through a pressure regulator and metering valve to control flow at a constant rate of 1,000–1,100 cc per minute and 1 atm pressure. The refrigerant vapor was fed to another copper tube 180 cm in length and 0.635 cm outer diameter formed into a U-shape placed in a constant temperature bath. The U-shaped tube (U-tube) began with a straight vertical section 37 cm long then bent to a horizontal section 27 cm long at the bottom of the bath. The tube then rose vertically in a zig-zag pattern with four 23 cm lengths, followed by another vertical straight section 23 cm long. The U-tube was filled with 10 grams of oil, optionally containing oil-return agent and oil-return-agent carrier, which was added to the U-tube through the 37 cm vertical tube. Vapor refrigerant passed slowly through the oil in the U-tube. Refrigerant and oil exiting the U-tube was collected in a receiver and refrigerant allowed to evaporate. Oil was then weighed to determine how much was carried out of the U-tube by the refrigerant.

R407C refrigerant (23 weight % HFC-32, 25 weight % HFC-125 and 52 weight % HFC-134a) was placed in the refrigerant cylinder. Suniso® 3GS mineral oil was placed in the copper U-tube, wherein total oil and oil-return agent, and oil-return-agent carrier equaled 10 grams. The constant temperature bath was held at a temperature of 0° C. Refrigerant vapor was fed through the U-tube at a flow rate of 1,100 cubic centimeters per minute and weight of oil in the receiver measured at 6, 10, and 20 minute time intervals. Refrigerant compositions of the present invention were then tested with Suniso® 3GS. Data are shown in Table 7 below.

TABLE 7

Oil Return with 3GS Mineral Oil

| Refrigerant | Composition (Wt %) | Weight % of Oil Returned | | |
|---|---|---|---|---|
| | | 6 Min | 10 Min | 20 Min |
| R407C (HFC-32/HFC-125/HFC-134a) | 23/25/52 | 11.1 | 22.3 | 32.3 |
| HFC-32/HFC-125/HFC-134a/n-butane | 10/45/42.5/2.5 | 12.9 | 25.2 | 32.9 |
| HFC-32/HFC-125/HFC-134a/isobutane | 10/47/40.5/2.5 | 12.5 | 23.0 | 34.2 |
| HFC-32/HFC-125/HFC-134a/n-butane/2-methyl butane | 5/32/60/2/1 | 16.1 | 26.9 | 35.5 |
| HFC-32/HFC-125/HFC-134a/n-butane/n-pentane | 1/60/34/4/1 | 22.5 | 31.5 | 39.7 |
| HFC-32/HFC-125/HFC-134a/isobutane/2-methylbutane | 14.5/24/60/1.0/0.5 | 12.1 | 23.0 | 32.4 |
| HFC-32/HFC-125/HFC-134a/isobutane/n-pentane | 19/50/30/0.5/0.5 | 13.8 | 24.2 | 33.5 |
| HFC-32/HFC-125/HFC-134a/n-butane with enhanced 3GS* | 10/45/42.5/2.5 | 28.2 | 33.3 | 38.4 |
| HFC-32/HFC-125/HFC-134a with enhanced 3GS* | 10/45/45 | 28.5 | 33.0 | 38.1 |

* 3GS oil is enhance with 0.4 wt % Zonyl®PHS plus 3% Isopar®H plus 200 ppm Dow 200 antifoam agent. Zonyl®PHS is sold by E.I. du Pont de Nemours & Co. and is a random copolymer made from 40 weight percent $CH_2=C(CH_3)CO_2CH_2CH_2(CF_2CF_2)_{m'}F$, wherein m' is from 1 to 12, primarily 2 to 8, and 60 weight percent lauryl methacrylate $(CH_2=C(CH_3)CO_2(CH_2)_{11}CH_3)$. Isopar®H is a high purity iso-parafinic hydrocarbon with low aromatics sold by Exxon Chemical Results from Example 6 show in all cases, oil return of the compositions of the present invention is improved versus R407C. Oil return increases with increased hydrocarbon concentration. Addition of polymeric oil return agent Zonyl®PHS to 3GS oil further improves oil return.

What is claimed is:

1. A nonflammable, azeotrope-like composition consisting essentially of from about 1 to about 19 weight percent difluoromethane (HFC-32), from about 25 to about 60 weight percent pentafluoroethane (HFC-125), from about 24 to about 60 weight percent 1,1,1,2-tetrafluoroethane (HFC-134a) and from about 0.5 to about 5 weight percent of a hydrocarbon selected from the group consisting of: n-butane; isobutane; n-butane and 2-methylbutane; n-butane and n-pentane; isobutane and 2-methylbutane; and isobutane and n-pentane.

2. The azeotrope-like composition of claim 1 consisting essentially of from about 1 to about 15 weight percent difluoromethane (HFC-32), from about 30 to about 50 weight percent pentafluoroethane (HFC-125), from about 30 to about 50 weight percent 1,1,1,2-tetrafluoroethane (HFC-134a) and from about 1 to about 4 weight percent of said hydrocarbon.

3. The azeotrope-like composition of claim 1 consisting essentially of from about 1 to about 9 weight percent difluoromethane (HFC-32), from about 30 to about 50 weight percent pentafluoroethane (HFC-125), from about 30 to about 50 weight percent 1,1,1,2-tetrafluoroethane (HFC-134a) and from about 1 to about 4 weight percent of said hydrocarbon.

4. The azeotrope-like composition of claim 1, wherein the hydrocarbon is from about 0.5 to about 5 weight percent of:

a) n-butane, said azeotrope-like composition having a vapor pressure of from about 979 kPa to about 1348 kPa at a temperature of about 25° C.; or b) isobutane, said azeotrope-like composition having a vapor pressure of from about 985 kPa to about 1351 kPa at a temperature of about 25° C.; or c) n-butane and 2-methylbutane, said azeotrope-like composition having a vapor pressure of from about 974 kPa to about 1342 kPa at a temperature of about 25° C.; or d) n-butane and n-pentane, said azeotrope-like composition having a vapor pressure of from about 973 kPa to about 1341 kPa at a temperature of about 25° C.; or e) isobutane and 2-methylbutane, said azeotrope-like composition having a vapor pressure of from about 976 kPa to about 1345 kPa at a temperature of about 25° C.; or f) isobutane and n-pentane, said azeotrope-like composition having a vapor pressure of from about 975 kPa to about 1344 kPa at a temperature of about 25° C., and wherein after 50 weight percent of said azeotrope-like composition has evaporated, the vapor pressure of the remaining composition has changed by about 10 percent or less.

5. A process for producing refrigeration, comprising condensing a composition of claims 1, 2, 3, or 4, and thereafter evaporating said composition in the vicinity of the body to be cooled.

6. A process for producing heat, comprising condensing a composition of claims 1, 2, 3, or 4, in the vicinity of the body to be heated, and thereafter evaporating said composition.

* * * * *

UNITED STATES PATENT AND TRADEMARK OFFICE
CERTIFICATE OF CORRECTION

| | |
|---|---|
| PATENT NO. | : 6,783,691 B1 |
| DATED | : August 31, 2004 |
| INVENTOR(S) | : Bivens Donald Bernard, Minor Barbara Haviland and Yokozeki Akimichi |

It is certified that error appears in the above-identified patent and that said Letters Patent is hereby corrected as shown below:

<u>Title page,</u>
Item [22] PCT Filed, replace "Mar. 20, 2000" with -- Mar. 21, 2000 --

Signed and Sealed this

Thirty-first Day of May, 2005

JON W. DUDAS
*Director of the United States Patent and Trademark Office*